(12) United States Patent
Respini et al.

(10) Patent No.: US 9,581,581 B2
(45) Date of Patent: Feb. 28, 2017

(54) METHODS OF DETERMINING CRUDE OIL STABILITY

(71) Applicant: Baker Hughes Incorporated, Houston, TX (US)

(72) Inventors: Marco Respini, Casalmorano (IT); Giuseppe Della Sala, Liverpool (GB); Gavin M. Medine, Amsterdam (NL); Corina L. Sandu, Pearland, TX (US)

(73) Assignee: Baker Hughes Incorporated, Houston, TX (US)

( * ) Notice: Subject to any disclaimer, the term of this patent is extended or adjusted under 35 U.S.C. 154(b) by 5 days.

(21) Appl. No.: 14/690,012

(22) Filed: Apr. 17, 2015

(65) Prior Publication Data

US 2015/0219614 A1 Aug. 6, 2015

Related U.S. Application Data

(63) Continuation-in-part of application No. 13/924,089, filed on Jun. 21, 2013, now Pat. No. 9,377,450.
(Continued)

(51) Int. Cl.
*G01N 21/41* (2006.01)
*G01N 33/28* (2006.01)
(Continued)

(52) U.S. Cl.
CPC ......... *G01N 33/2823* (2013.01); *C10G 31/08* (2013.01); *C10G 33/04* (2013.01); *C10G 75/00* (2013.01); *G01N 21/41* (2013.01); *G01N 21/552* (2013.01); *C10G 2300/206* (2013.01); *G01N 21/83* (2013.01); *G01N 21/8507* (2013.01); *G01N 2021/8416* (2013.01); *Y10T 137/0324* (2015.04)

(58) Field of Classification Search
CPC .. G01N 33/2823; G01N 21/552; G01N 21/41; G01N 21/83; G01N 21/8507; G01N 2021/8416; C10G 33/04; C10G 75/00; C10G 31/08; C10G 2300/206; Y10T 137/0324
See application file for complete search history.

(56) References Cited

U.S. PATENT DOCUMENTS

| 5,871,634 A | 2/1999 | Wiehe et al. |
| 5,997,723 A | 12/1999 | Wiehe et al. |

(Continued)

OTHER PUBLICATIONS

Andersen, S., "Flocculation Onset Titration of Petroleum Asphaltenes," Energy and Fuels, vol. 13, pp. 315-322 (1998).
(Continued)

*Primary Examiner* — Randy Boyer
*Assistant Examiner* — Juan Valencia
(74) *Attorney, Agent, or Firm* — Mossman, Kumar & Tyler, P.C.

(57) ABSTRACT

The stability of an oil-based fluid crude oil fluid may be determined by measuring a first RI value of the crude oil that does not comprise a solvent where the first RI value is used to determine a first solubility parameter therefrom. A second RI value may be taken from the crude oil at a point of asphaltene flocculation during a turbidimetric flocculation titration. The second RI value may be used to determine a second solubility parameter. A process for refining the crude oil may be controlled by maintaining the process or implementing a change to the process based on a ratio of the first solubility parameter to the second solubility parameter.

19 Claims, 1 Drawing Sheet

Related U.S. Application Data

(60) Provisional application No. 61/663,441, filed on Jun. 22, 2012.

(51) Int. Cl.
*C10G 31/08* (2006.01)
*C10G 75/00* (2006.01)
*G01N 21/552* (2014.01)
*C10G 33/04* (2006.01)
*G01N 21/85* (2006.01)
*G01N 21/84* (2006.01)
*G01N 21/83* (2006.01)

(56) References Cited

U.S. PATENT DOCUMENTS

| 8,236,564 B2 | 8/2012 | Pauli et al. |
| 2010/0163461 A1 | 7/2010 | Wright et al. |
| 2012/0125087 A1 | 5/2012 | Sandu et al. |

OTHER PUBLICATIONS

Buckley, J.S. et al., "Asphaltene Precipitation and Solvent Properties of Crude Oils," Petroleum Science and Technology, vol. 16 (3 & 4), pp. 251-285 (1998).
ASTM Designation D7157-12: Standard Test Method for Determination of Intrinsic Stability of Asphaltene-Containing Residues, Heavy Fuel Oils and Crude Oils (n-Heptane Phase Separation; Optical Detection)(Feb. 2013).
Wang, Jianxin et al., New Mexico Petroleum Recovery Research Center, PRRC 01-18, Procedure for Measuring the Onset of Asphaltene Flocculation (2001).

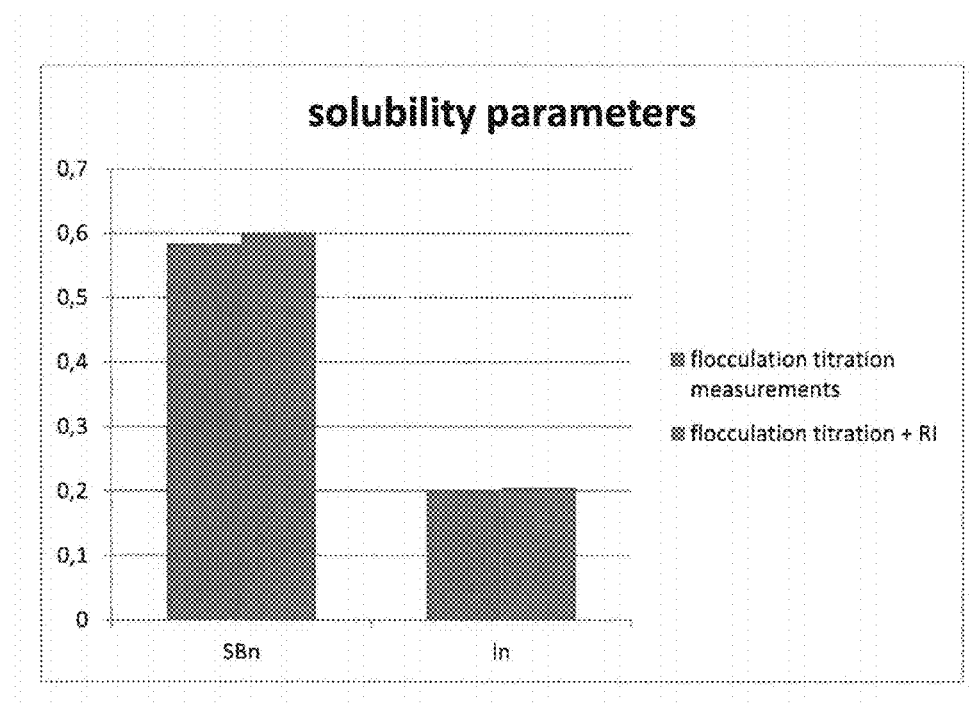

METHODS OF DETERMINING CRUDE OIL STABILITY

CROSS REFERENCE TO RELATED APPLICATIONS

This application is a Continuation-in-Part and claims priority to U.S. application Ser. No. 13/924,089 filed on Jun. 21, 2013; which claims priority to U.S. Provisional Application Ser. No. 61/663,441 filed on Jun. 22, 2012; all of which are incorporated by reference herein in their entirety.

TECHNICAL FIELD

The present invention relates to determining a stability of a crude oil by measuring a first refractive index (RI) value of a crude oil that does not comprise solvent to determine a first solubility parameter therefrom, measuring a second RI value of a crude oil comprising a solvent during a turbidimetric flocculation titration, where the second RI value is measured at a point of asphaltene flocculation to determine a second solubility parameter, and controlling the process for refining crude oil by maintaining the process or implementing a change to the process based on a ratio of the first solubility parameter to the second solubility parameter.

BACKGROUND

As world reserves of light, sweet crudes diminish and worldwide consumption of oil increases, refiners seek methods for extracting useful products such as gasoline and fuel oils from heavier crude resources. While not as desirable and easy to process, extensive reserves in the form of "heavy crudes" exist in a number of countries, including Western Canada, Venezuela, Russia, the United States, and elsewhere.

For example, heavy or extra heavy crude oil can be found in the Orinoco Belt in Venezuela, the oil sands in Canada, and the Ugnu Reservoir in Northern Alaska. Alberta produces approximately two-thirds of Canada's oil and more than three-quarters of its natural gas. Nearly half of Alberta's oil is mined from vast oil sands, which contain deposits of a heavy crude oil called bitumen. Alberta's oil sands represent the largest known deposits of bitumen in the world. The oil sands occur in three major areas of the province: the Athabasca River Valley in the northeast, the Peace River area in the north, and the Cold Lake region in east central Alberta.

Such heavy oils (even some not so heavy oils) are often difficult to refine because of their viscosity and propensity for being unstable and precipitating solids, such as asphaltenes, upon storage and processing, most notable asphaltenes. Asphaltenes are most commonly defined as that portion of petroleum, which is soluble in xylene and toluene, but insoluble in heptane or pentane. Asphaltenes exist in crude oil as both soluble species and in the form of colloidal dispersions stabilized by other components in the crude oil. Asphaltenes have higher molecular weights and are the more polar fractions of crude oil, and can precipitate upon pressure, temperature, and compositional changes in crude oil resulting from blending or other mechanical or physicochemical processing. Asphaltene precipitation and deposition can cause problems in subterranean reservoirs, upstream production facilities, mid-stream transportation facilities, refineries, and fuel blending operations. In petroleum production facilities, asphaltene precipitation and deposition can occur in near wellbore reservoir regions, wells, flowlines, separators, and other equipment.

When asphaltenes precipitate from crude oil, they can foul equipment and reduce the quality of the products being refined. Other issues associated with heavy crude oil include: high solids; increased amounts of entrained water; and high sulfur content; high total acid number (TAN) and high metals. Asphaltene deposition is a well-known problem affecting all aspects of petroleum production and processing. Crude oils containing high or low levels of asphaltenes can be destabilized while processing causing fouling, formation of sludge, corrosion and all the equipment fixing, cleaning, and cost aggravations associated with these effects.

Additional operational problems observed with heavy crude oil: difficulty in blending crude streams, increased unit upsets, increased pollution, loss of through-put, difficulty with desalting, increased load on wastewater plants, increase in air emissions, and flexibility in plant operations is reduced. All of this leads to an overall increase in operating costs.

Asphaltenes may be present and stable in a crude oil under equilibrium reservoir conditions, but may aggregate or deposit as temperatures, pressures, and overall fluid compositions change as the crude oil is removed from the reservoir during production and/or being further refined. Asphaltenes are typically dark brown to black-colored amorphous solids with complex structures and relatively high molecular weights.

Asphaltene stability can even be disturbed by mixing hydrocarbon-based fluids i.e. such as mixing two types of crude oils together, two types of shale oils together, condensates, and others, of different origins at certain ratios as the chemistry of the hydrocarbon-based fluids from different sources may be incompatible and induce destabilization of the asphaltenes therein. In non-limiting examples, such as during refining or fuel blending, two or more hydrocarbon-based fluids may be mixed together. Sometimes, changes in physical conditions are sufficient to induce destabilization, or even the mixture of different hydrocarbon-based fluids that have incompatible chemistries. Said differently, even if neither hydrocarbon-based fluid, alone, has destabilized foulants or the hydrocarbon-based fluid would not act as a destabilizing additive by itself, the mixing or the mixture of two or more hydrocarbon-based fluids may further destabilize the foulants present in either hydrocarbon-based fluid.

There are several shortcomings when measuring asphaltene stability to improve foulant stability. Thus, it would be desirable to develop better methods of analyzing the stability of the asphaltenes within crude oils.

SUMMARY

There is provided, in one form, a method for determining a stability of a crude oil by measuring a first refractive index (RI) value and a second RI value of the crude oil. The crude oil may not include a solvent during the first RI measurement. The second RI measurement may be taken at a point of asphaltene flocculation during a turbidimetric flocculation titration. The first RI and the second RI values may be used to determine a first solubility parameter and second solubility parameter respectively. A ratio of the first and second solubility parameters may be used to control a process for refining crude oil by maintaining the process or implementing a change to the process based on the ratio.

In an alternative non-limiting embodiment of the method, the crude oil may be a crude oil blend having at least two crude oils. The ratio of the first solubility parameter and second solubility parameter may be used to model asphaltenic phase behavior within the crude oil using a Flory Huggins or Hildebrand equation.

In another non-limiting embodiment, a laser light may be passed through the crude oil during the turbidimetric flocculation titration where the laser light has a wavelength ranging from about 800 nm independently to about 2500 nm. In addition, the first RI value and the second RI value may be measured at a location, such as but not limited to, upstream from a desalter, in a desalter, in a heat exchanger upstream from a desalter, in a pre-heater between a desalter and a furnace, and combinations thereof.

BRIEF DESCRIPTION OF THE DRAWING

FIG. 1 is a graph illustrating the first and second solubility parameters obtained by using turbidimetric flocculation titration, alone, with the same parameters obtained using turbidimetric flocculation titration in combination with refractive index values.

DETAILED DESCRIPTION

It has been discovered that the stability of asphaltenes within a crude oil may be measured. In a non-limiting embodiment, the crude oil may be a crude oil blend having at least two crude oils. To measure the stability of the asphaltenes therein, a first refractive index (RI) measurement may be taken with a refractive index probe inserted into the crude oil stream (or a crude oil sample) when the crude oil is undiluted, i.e. the crude oil does not include a solvent. The first RI measurement may be used to determine a first functional refractive index ($F_{RI}$) value by using the formula $F_{RI}=(RI^2-1)/(RI^2+2)$ where RI is the first refractive index measurement in this instance. The first $F_{RI}$ value may determine a first solubility parameter, also known as a solubility blending number (SBn), by using the formula $\delta=52.042F_{RI}+2.904$ (2) where $\delta$ is in units of 0.5 MPa where a linear correlation between the solubility parameter, $\delta$, and FRI at 20° C. may be established.

This correlation was established based on the one-third rule relating to the function of the refractive index divided by the mass density as a constant equal to ⅓ for all different compounds. This rule was validated on more than 229 crude oils at 20° C. as well as higher temperatures up to 80° C.

U.S. patent application Ser. No. 13/924,089 filed Jun. 22, 2012 discusses RI parameters measured online using a refractive index probe to convert the RI values into a "solubility blending number" (SBn) based on a linear correlation. The linear correlation may be established using any method known in the art, such as, for example, that disclosed in the method published by the New Mexico Petroleum Recovery Research Center as PRRC 01-18. This document, authored by Jianxin Wang and Jill Buckley and having the title: Procedure for Measuring the Onset of Asphaltenes Flocculation.

A second refractive index (RI) measurement may be taken with a refractive index probe inserted into the crude oil stream (or a crude oil sample) during a turbidimetric flocculation titration, i.e. the crude oil undergoes a series of dilutions with a solvent to induce asphaltene precipitation. At the point when crude oil begins precipitating asphaltenes, also known as asphaltene flocculation, a second RI measurement may be taken to determine a second $F_{RI}$ value and thereby determine a second solubility parameter. The second RI measurement may be used to determine the second $F_{RI}$ value. The second solubility parameter may be an insolubility number (In).

After obtaining the first solubility parameter of the crude oil and obtaining the second solubility parameter of the crude oil, a process for refining crude oil may be monitored for better control of the process. Based on the ratio of the first solubility parameter to the second solubility parameter, the process may be maintained, or a change may be implemented to the process. In a non-limiting embodiment, the process may be maintained if the ratio falls within a pre-determined range, or the process may be changed if the ratio falls outside a pre-determined ratio.

In a non-limiting embodiment, the asphaltenic behavior within the crude oil may be modeled using a Flory Huggins or Hildebrand equation. The Flory Huggins solution theory is a model of the thermodynamics of polymer solutions that takes account of the great dissimilarity in molecular sizes in adapting the usual expression for the entropy of mixing. The Hildebrand solubility parameter provides a numerical estimate of the degree of interaction between materials, and can be a good indication of solubility, particularly for nonpolar materials such as polymers.

The asphaltenes may be modeled as polymers in a solvent where the solvent is the crude oil matrix. The precipitation of asphaltenes may be driven by the difference of solubility parameters between asphaltenes and oil, as well as by the molecular weight of asphaltenes. If the solubility parameter difference between the asphaltenes and oil is too high, e.g. above 2 to 2.5 $cal^{1/2}$ $cm^{-3/2}$ in a non-limiting example, asphaltenes will precipitate. The Flory Huggins and/or Hildebrand models allow for calculation of the solubility limit of asphaltenes starting from the solubility parameters and incorporating temperature and pressure. The solubility parameters may be changed by temperature, pressure and by adding solvents (or precipitants) to the oil. The way a particular crude oil reacts to changes in pressure, temperature and/or adding other crude oils thereto may be predictable based on the thermodynamics of the particular crude oil. The asphaltenic behavior may also be predicted in this manner.

The equation for the Hildebrand solubility parameter is $$\delta = \sqrt{\frac{\Delta H_c - RT}{V_m}}.$$

During the tubidimetric flocculation titration, a laser light may be passed through the crude oil where the laser light has a wavelength ranging from about 800 nm independently to about 2500 nm. Alternatively, the wavelength of light may range from about 1000 nm independently to about 2000 nm, or from about 1300 nm independently to about 1800 nm in another non-limiting embodiment. The turbidimetric flocculation titration may occur with a turbidimetric method, such as but not limited to turbidimetry, nephelometry, infrared spectroscopy by attenuated total reflectance (ATR), and combinations thereof. The solvent for the turbidimetric flocculation titration may be or include, but is not limited to, cetane, heptane, xylene, toluene, hexane, pentane, methylnaphthalene, a paraffinic solvent having a solubility range of about 6.8 to 7.2 $(cal/cm3)^{1/2}$, and combinations thereof.

Turbidimetry is a process of measuring the loss of intensity of transmitted light due to the scattering effect of particles suspended therein. Light may be passed through a filter creating a light of known wavelength that is then passed through a cuvette containing a solution.

Nephelometry uses a nephelometer to measure the concentration of suspended particulates in a liquid or gas colloid by employing a light source and a light detector set to one side (e.g. 90 degrees) of the light source beam. Particle density may be a function of light reflected into the detector from the particles. The reflected light may be dependent upon properties of the particles, such as shape, color, and reflectivity.

Attenuated total reflectance is a sampling technique used in conjunction with infrared spectrometry to examine solid or liquid states of samples without further preparation. ATR uses a property of total internal reflection resulting in an evanescent wave. An infrared light beam may be passed through an ATR crystal to reflect at least once off the internal surface in contact with the sample. The reflection forms the evanescent wave that extends into the sample. The penetration depth into the sample may be determined by the wavelength of light, the angle of incidence and the indices of refraction for the ATR crystal and the medium being probed. The ATR crystal may be made of an optical material with a higher refractive index than the sample being studied.

In a non-limiting embodiment, the turbidimetric flocculation titration method may be an optical method using a coherent light source that allows measuring the transmittance through the sample and relates especially to measuring the onset flocculation of asphaltenes within a crude sample. Changes in the sample transmittance (such as asphaltene aggregation and precipitation) may be induced via temperature and/or via adding a solvent. The transmittance changes versus temperature and/or solvent addition may be measured with high degree of sensitivity and repeatability.

The three dilution approach may be used. Crude sample of known amounts may be diluted at three different ratios: 1:1, 1:2, 1:1.5, and so on until asphaltenes begin precipitating from the crude oil sample in a non-limiting embodiment. At each dilution, a refractive index measurement may be taken, and the refractive index measurement may be plotted on the x-axis, and its respective SBn value may be plotted on the y-axis.

In a non-limiting embodiment, the crude oil may be heated prior to obtaining the first solubility parameter to decrease the viscosity of the crude oil. The temperature of the crude oil during the heating thereof may range from about 20 C independently to about 250 C, alternatively from about 50 C independently to about 100 C.

The solubility parameters may be employed to determine whether a particular stream may be transported, blended, stored, refined, and combinations thereof. Since solubility parameters are rarely alike for two crudes, the operator of any refinery or pipeline or storage facility may use the solubility parameters to determine the stability of the crude oil in particular equipment and/or systems. Variables in these systems include, pipe lines and storage facilities, pipe diameter, stream temperature, stream velocity, and the availability and type of agitation or stirring present, if any. For a refining unit, variables influencing the stability of the crude oil may include the ability to heat the process streams and residence time inside of reactors, reformers, cokers and other types of refinery equipment.

If a crude oil has a ratio within the range for the pre-determined ratio of the first solubility parameter to the second solubility parameter, then the operator may elect to maintain the process within a refinery. The pre-determined ratio may range from about 1.9 independently to about 2.5, alternatively from about 2 independently to about 2.5, or 2.2 independently to about 2.3. If the measured ratio falls outside of the pre-determined ratio, then the operator may elect to change the process within a refinery.

Often though, it may be desirable to implement a change to the process, change the crudes to be blended, change the crude mixing order, add chemical solutions to prevent fouling, etc. In one non-limiting embodiment of the method of the application, the operator may elect to change operating parameters including, but not limited to changing fluid flow velocities, changing unit operating temperatures, changing unit residence times, and the like.

In another non-limiting embodiment, the operator may elect to make changes by mixing at least two feed streams to bring the ratio of the solubility parameters of the combined stream into the pre-determined range. In some embodiments, the second feed stream may not even be crude oil. For example, a refinery may elect to use a lighter feed stock such as gas oil, paraffinic feed, lighter cutter stocks, etc. that could be recovered and recycled.

In yet another embodiment, the mixing or blending of feed streams may be the blending of streams that are often prone to problems. One such is the blending of heavy crude oil and shale oil. Shale oil is paraffinic and is often prone to blending problems.

In combining or blending feed streams, any method of performing this function may be employed. For example, the feed streams may be introduced into a tank and agitated. In an alternative embodiment, the feed streams may be co-injected into a line having static mixers in place. In still another embodiment, both methods may be employed to mix crude oil feed streams to prepare a crude oil feed stream.

When the ratio of solubility parameters is not within the pre-determined range, remedial efforts may be employed to mitigate the instability of the crude oil. At least one such remedial effort may include using a stabilizing additive. Any additive known to be useful to those of ordinary skill in the art may be employed with the method of the application. For example, in one embodiment, the additive may be prepared from a formulation including: a first component selected from the group consisting of (alkoxylated)-(di or tri)-alkyl phenol-aldehyde (amine) resins; α-Olefin-maleic anhydride co-polymers and grafted polymers including half ester/amide and full ester/amide derivatives; and combinations thereof. Such a formulation may also include a second component that may be or include, but is not limited to, polyamines, amidoamines, imidazolines, and combinations thereof.

The additives useful with the methods of the application may increase the stability of the crude oil. Such stability additives may be employed at a concentration ranging from about 0.025 independently to about 10 wt %, alternatively from about 0.1 independently to about 5 wt %, or from about 1 independently to about 4 wt %.

The ratio of first and second parameters may be used to determine crude oil stability when crude oil is being transported, moved or processed. It would be desirable to avoid destabilization of the crude oil after transportation and storage, and/or processing once precipitation of the asphaltenes and aggregation is formed.

A titration need only be performed periodically, sometimes as infrequently as once per "batch" of crude oil to determine the second solubility parameter. Of course, in some embodiments wherein large batches of crude oil are being transported or stored or blended, it may be desirable to run this test more frequently. Generally speaking though, once the SBn and/or In have been determined, these values do not tend to change absent a substantial change to the conditions and/or quality of the crude oil.

In a non-limiting embodiment, a refractive index probe may be deployed at a location suitable for making a crude oil stability determination where the crude oil stability determination is relevant to controlling the refining process. In one embodiment, it may be desirable to place a RI probe into the feed going into a desalting unit. As crude oil comes into the refinery tankage, it generally contains sand, minerals, and salts plus iron oxides that have flaked off equipment during transportation. All of these may cause fouling during the refining process.

Much of this material will settle out in the crude oil tanks, but the salt is mostly in tiny droplets of water dispersed throughout the crude oil. Much of this water will not drop out with just settling, so desalting is carried out in desalting units. Some of these units function by adding fresh water to the crude. In many cases, the water will dissolve almost all the salt and then drop to the bottom of the desalter for removal. In other, more stubborn situations, the crude oil is passed through a high voltage electrical field that is sometimes as high as 12,000 to 35,000 volts. That causes the tiny, salt laden water droplets to coalesce and then settle out.

When going through a desalter, crude oil may be subjected to a change in temperature. In some instances, this is sufficient to destabilize crude oil. By placing an RI probe at this point of a refinery process and determining the first solubility parameter (SBn) and second solubility parameter (In) to compare the two as a ratio, an operator may be warned of the onset of fouling and could then take mitigating steps. In one non-limiting embodiment, the operator may elect to add an additional feed stream to the desalter where the additional feed stream may stabilize the first feed stream. In an alternative non-limiting embodiment, the operator may employ an additive, select a demulsifier with a different charge, or change the temperature or water feed rate of the desalting unit.

Upstream of a desalting unit in most refineries is a heat exchanger often called a cold train. In some embodiments of the method of the application, it may be desirable to place an RI probe at this location process and determine the first solubility parameter (SBn) and second solubility parameter (In) to compare the two as a ratio. An operator may then mitigate fouling by increasing temperatures, employing additives, or increasing the sheer forces on the crude oil as it passes through the exchanger.

Yet another location for an RI probe may be the pre-heater located between the desalter and first furnace. By determining the first solubility parameter (SBn) and second solubility parameter (In) to compare the two as a ratio at this location, an operator mitigate fouling downstream, by adjusting the temperature of the pre-heater or employ additives. Determining the first solubility parameter (SBn) and second solubility parameter (In) to compare the two as a ratio may occur at any location within a refinery where a determination of SBn and/or In could be useful in mitigating fouling.

In methods of the application related to the storage and transportation of crude oil, it may be desirable to employ an RI probe in a sample loop or directly in a crude oil storage tank to determine the first solubility parameter (SBn) and second solubility parameter (In) to compare the two as a ratio at this location. To mitigate fouling, an operator may elect to feed more stable crude oil, increase agitation and/or stirring, employ additives, and combinations thereof.

In another non-limiting embodiment, the first solubility parameter (SBn) and second solubility parameter (In) may be determined and compared as a ratio to properly ratio a blend of crude oils entering into a storage vessel to produce a batch of crude oil to use as a feed stream for a refinery. In another non-limiting embodiment, the ratio of first solubility parameter (SBn) and second solubility parameter (In) may allow for better monitoring of homogenization of the contents of the crude oil storage vessel.

As noted from the graph, the titration measurements in combination with the RI measured values are more accurate representations of the first and second solubility parameter values than the titration values, alone.

The invention will be further described with respect to the following Examples, which are not meant to limit the invention, but rather to further illustrate the various embodiments.

EXAMPLES

Example 1

Now turning to the FIGURE, FIG. 1 is a graph illustrating the first and second solubility parameters obtained by using turbidimetric flocculation titration, alone, with the same parameters obtained using turbidimetric flocculation titration in combination with refractive index values. As already noted, the turbidimetric flocculation titration includes adding a non-solvent to crude oil and determining the onset flocculation of asphaltenes. It is routine to make at least 3 measurements requiring from 60 minutes to two hours to dependably make solubility parameter determination using this method. This delay has in the past precluded the use of SBn as a real time measurement for control of a refining or transportation and storage process. In addition, there is another limiting component.

The crude oil used to perform the titration, alone, (displayed as the left bar for the first and second solubility parameters) was the same crude oil used for the titration and RI combination. The titration has been explained. For the right bar displayed for the first and second solubility parameters, the RI value was obtained prior to the dilution of the crude oil for the first solubility parameter (i.e. SBn), and the RI value was obtained at the onset of asphaltene flocculation during the turbidimetric flocculation titration for the second solubility parameter (i.e. In). The first and second RI values were then used to determine their respective first and second FRI values for subsequent determination of their respective first and second solubility parameters.

In the foregoing specification, the invention has been described with reference to specific embodiments thereof, and has been described as effective in providing methods determining a stability of a crude oil. However, it will be evident that various modifications and changes can be made thereto without departing from the broader spirit or scope of the invention as set forth in the appended claims. Accordingly, the specification is to be regarded in an illustrative rather than a restrictive sense. For example, specific crude oils, solvents, dispersants, asphaltene inhibitors, additives, tubridimetry methods, and wavelengths of laser light falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method for determining a stability of a crude oil may consist of or consist essentially of measuring a first refractive index (RI) value and a second RI value of the crude oil; the crude oil may not include a solvent during the first RI measurement; the second RI measurement may be taken at a point of asphaltene flocculation during a turbidimetric flocculation titration; the first RI and the second RI values may be used to determine a first solubility parameter and second solubility parameter respectively; a ratio of the first and second solubility parameters may be used to control a process for refining crude oil by maintaining the process or implementing a change to the process based on the ratio The words "comprising" and "comprises" as used throughout the claims, are to be interpreted to mean "including but not limited to" and "includes but not limited to", respectively.

What is claimed is:

1. A method for determining a stability of a crude oil to control a process for refining a crude oil comprising:
    measuring a first refractive index (RI) value of the crude oil that does not comprise a solvent; wherein the first RI value is used to determine a first solubility parameter;
    measuring a second RI value of the crude oil at a point of asphaltene flocculation during a turbidimetric flocculation titration; wherein the second RI value is used to determine a second solubility parameter; and
    controlling a process for refining crude oil by maintaining the process or implementing a change to the process based on a ratio of the first solubility parameter to the second solubility parameter; wherein implementing a change to the process is selected from the group consisting of:
        adding an additional feed stream to the crude oil to stabilize the crude oil;
        changing an operating temperature of one or more units in a refining process;
        adding an additive to the crude oil;
        adding a different demulsifier to the crude oil than any demulsifier already present in the crude oil;
        changing a temperature of the crude oil;
        changing a water feed rate of a desalting unit;
        and combinations thereof.

2. The method of claim 1, wherein the crude oil is a crude oil blend comprising at least two crude oils.

3. The method of claim 1 further comprising modeling asphaltenic phase behavior within the crude oil using a Flory Huggins or Hildebrand equation.

4. The method of claim 1, wherein a laser light is passed through the crude oil during the turbidimetric flocculation titration; and wherein the laser light has a wavelength ranges from about 800 nm to about 2500 nm.

5. The method of claim 1, wherein the turbidimetric flocculation titration occurs with a turbidimetric method selected from the group consisting of turbidimetry, nephelometry, infrared spectroscopy by attenuated total reflectance (ATR), and combinations thereof.

6. The method of claim 1, wherein the first RI value and the second RI value are measured at a location selected from the group consisting of upstream from a desalter, in a desalter, in a heat exchanger upstream from a desalter, in a pre-heater between a desalter and a furnace, and combinations thereof.

7. The method of claim 2, wherein implementing a change to the process comprises changing a blending process for creating the crude oil blend.

8. The method of claim 1 further comprising heating the crude oil prior to obtaining the first solubility parameter to decrease the viscosity of the crude oil.

9. The method of claim 1, wherein the turbidimetric flocculation titration comprises the use of a solvent selected from the group consisting of cetane, heptane, xylene, toluene, hexane, pentane, methylnaphthalene, a paraffinic solvent having a solubility range of about 6.8 to 7.2 $(cal/cm^3)^{1/2}$, and combinations thereof.

10. A method for determining a stability of a crude oil blend comprising at least two crude oils control a process for refining a crude oil; wherein the method comprises:
    measuring a first refractive index (RI) value of the crude oil blend that does not comprise a solvent; wherein the first RI value is used to determine a first solubility parameter;
    measuring a second RI value of the crude oil blend at a point of asphaltene flocculation during a turbidimetric flocculation titration; wherein the second RI value is used to determine a second solubility parameter;
    controlling a process for refining crude oil by maintaining the process or implementing a change to the process based on a ratio of the first solubility parameter to the second solubility parameter equation, wherein implementing a change to the process is selected from the group consisting of:
        adding an additional feed stream to the crude oil to stabilize the crude oil;
        changing an operating temperature of one or more units in a refining process;
        adding an additive to the crude oil;
        adding a different demulsifier to the crude oil than any demulsifier already present in the crude oil;
        changing a temperature of the crude oil;
        changing a water feed rate of a desalting unit;
        and combinations thereof; and
        modeling asphaltenic phase behavior within the crude oil using a Flory Huggins or Hildebrand.

11. The method of claim 10, wherein a laser light is passed through the crude oil during the turbidimetric flocculation titration; and wherein the laser light has a wavelength ranges from about 800 nm to about 2500 nm.

12. The method of claim 10, wherein the turbidimetric flocculation titration occurs with a turbidimetric method selected from the group consisting of turbidimetry, nephelometry, infrared spectroscopy by attenuated total reflectance (ATR), and combinations thereof.

13. The method of claim 10, wherein the first RI value and the second RI value are measured at a location selected from the group consisting of upstream from a desalter, in a desalter, in a heat exchanger upstream from a desalter, in a pre-heater between a desalter and a furnace, and combinations thereof.

14. The method of claim 10 further comprising heating the crude oil prior to obtaining the first solubility parameter to decrease the viscosity of the crude oil.

15. The method of claim 10, wherein the turbidimetric flocculation titration comprises the use of a solvent selected from the group consisting of cetane, heptane, xylene, toluene, hexane, pentane, methylnaphthalene, a paraffinic solvent having a solubility range of about 6.8 to 7.2 $(cal/cm3)^{1/2}$, and combinations thereof.

16. A method for determining a stability of a crude oil to control a process for refining a crude oil comprising:
    measuring a first refractive index (RI) value of the crude oil that does not comprise a solvent; wherein the first RI value is used to determine a first solubility parameter;
    measuring a second RI value of the crude oil at a point of asphaltene flocculation during a turbidimetric flocculation titration; wherein the second RI value is used to determine a second solubility parameter; wherein a laser light is passed through the crude oil during the turbidimetric flocculation titration; and wherein the laser light has a wavelength ranging from about 800 nm to about 2500 nm;

controlling a process for refining crude oil by maintaining the process or implementing a change to the process based on a ratio of the first solubility parameter to the second solubility parameter, wherein implementing a change to the process is selected from the group consisting of:

adding an additional feed stream to the crude oil to stabilize the crude oil;

changing an operating temperature of one or more units in a refining process;

adding an additive to the crude oil;

adding a different demulsifier to the crude oil than any demulsifier already present in the crude oil;

changing a temperature of the crude oil;

changing a water feed rate of a desalting unit;

and combinations thereof; and wherein the first RI value and the second RI value are measured at a location selected from the group consisting of upstream from a desalter, in a desalter, in a heat exchanger upstream from a desalter, in a preheater between a desalter and a furnace, and combinations thereof.

17. The method of claim 16, wherein the crude oil is a crude oil blend comprising at least two crude oils.

18. The method of claim 17, wherein implementing a change to the process comprises changing a blending process for creating the crude oil blend.

19. The method of claim 16 further comprising heating the crude oil prior to obtaining the first solubility parameter to decrease the viscosity of the crude oil.

* * * * *